US011417423B2

(12) United States Patent
Chen et al.

(10) Patent No.: US 11,417,423 B2
(45) Date of Patent: Aug. 16, 2022

(54) MULTI-COIL MAGNETIC RESONANCE IMAGING WITH ARTIFICIAL INTELLIGENCE

(71) Applicant: Shanghai United Imaging Intelligence Co., LTD., Shanghai (CN)

(72) Inventors: Xiao Chen, Cambridge, MA (US); Zhang Chen, Cambridge, MA (US); Shanhui Sun, Cambridge, MA (US); Terrence Chen, Cambridge, MA (US)

(73) Assignee: Shanghai United Imaging Intelligence Co., LTD., Xuhui District (CN)

( * ) Notice: Subject to any disclaimer, the term of this patent is extended or adjusted under 35 U.S.C. 154(b) by 85 days.

(21) Appl. No.: 16/986,787

(22) Filed: Aug. 6, 2020

(65) Prior Publication Data

US 2022/0044790 A1    Feb. 10, 2022

(51) Int. Cl.
*G16H 30/20* (2018.01)
*G06N 3/08* (2006.01)
*G01R 33/34* (2006.01)
*G01R 33/56* (2006.01)

(52) U.S. Cl.
CPC ............. *G16H 30/20* (2018.01); *G01R 33/34* (2013.01); *G01R 33/5608* (2013.01); *G06N 3/08* (2013.01)

(58) Field of Classification Search
USPC .......................................................... 324/309
See application file for complete search history.

(56) References Cited

U.S. PATENT DOCUMENTS

| 10,527,699 | B1* | 1/2020 | Cheng | G01R 33/5611 |
| 2013/0044960 | A1* | 2/2013 | Zhang | G01R 33/5611 382/232 |
| 2017/0169564 | A1* | 6/2017 | Hansen | G01R 33/56341 |
| 2019/0236817 | A1* | 8/2019 | Cheng | G06N 3/0454 |
| 2020/0294287 | A1* | 9/2020 | Schlemper | G06K 9/6203 |
| 2021/0003651 | A1* | 1/2021 | Kamiguchi | G06N 20/00 |
| 2021/0397966 | A1* | 12/2021 | Sun | G06N 3/084 |

* cited by examiner

*Primary Examiner* — Rodney E Fuller
(74) *Attorney, Agent, or Firm* — Ziegler IP Law Group, LLC

(57) ABSTRACT

A method includes acquiring magnetic resonance imaging (MRI) data with multi-coil dimensions, compressing the coil dimensions to a fixed and predetermined number of virtual coils, and utilizing the fixed and predetermined number of virtual coils by an artificial intelligence engine for artificial intelligence applications.

19 Claims, 4 Drawing Sheets

MULTI-COIL MAGNETIC RESONANCE IMAGING WITH ARTIFICIAL INTELLIGENCE

BACKGROUND

The aspects of the present disclosure relate generally to Magnetic Resonance imaging (MRI), and in particular to using coil compression to enable application of artificial intelligence methods to multi-coil MRI.

MRI is a widely used medical technique which produces images of a region of interest using magnetic and radio frequency energy. During an MRI scan, volume coils (for example, body coils) and local coils (for example, surface coils) may acquire MR signals produced by nuclear relaxation inside the object being examined.

Most MRI scanners use multiple receiving coils to collect spatially varying signals simultaneously, which greatly reduces scanning time and increases image quality. For a targeted image resolution and size, the use of multi-coil acquisition increases the size of the data collected by a factor of the number of coils. For example, a targeted image of $N_x \times N_y \times N_z$ will collect $N_x \times N_y \times N_z \times N_{coil}$ data, where $N_x$, $N_y$, $N_z$ are the spatial dimensions along the x, y, and z axes, respectively, and $N_{coil}$ is the number of coils. For contemporary MRI scanners, the coil number may be 64 or more, with a general rule that as the number of coils increase, so does image quality and acquisition speed. However, the increase in coils also results in a challenging amount of data to be processed for reconstruction and post-analysis.

Artificial intelligence, implemented for example using deep-learning (DL) based neural networks (NN), has gained much attention recently, given its huge success in general computer vision. Multiple DL methods are proposed for MRI image reconstruction and processing and has shown promising results. However, for practical implementation of the algorithms for MRI, the incoming data as inputs to the NN will have a large and unfixed coil dimension, as the user may choose any number of coils smaller than the system maximum. Most of the currently proposed DL methods require a specific input size and a larger coil dimension may require increased memory consumption during both inference and training, which may limit NN complexity and capability.

One solution to the variable coil dimension is to apply the DL method independently to each coil during training and inference. However, this may introduce several potential problems: 1) images of each coil during training may be quite different from those of testing because the position of the coils can be arbitrarily configured during a scan; 2) signals of each individual coil may be noisier and correlation between coils is ignored resulting in a difficult training problem; and 3) inference time is significantly increased as a result of applying the DL method to each coil independently.

Another solution may include combining multiple coil signals into a single combined coil image using coil sensitivity maps, however, this approach relies heavily on the quality of the estimation of the coil sensitivity maps.

SUMMARY

It would be advantageous to provide a method and system that provides a fixed coil dimension for artificial intelligence applications independent of the number of coils utilized during MR image acquisition.

According to an aspect of the present disclosure a method includes acquiring MRI data with multi-coil dimensions, compressing the coil dimensions to a fixed and predetermined number of virtual coils, and utilizing the fixed and predetermined number of virtual coils for artificial intelligence applications.

The method may include acquiring the MRI data with multi-coil dimensions from one or more of an MRI scanner, an MRI data storage, a k-space storage, or an image storage.

The multi-coil dimensions may include 12, 16, 24, 32, or 64 coils.

The fixed and predetermined number of virtual coils may be between 4 and 20.

The method may include compressing the coil dimensions to a fixed and predetermined number of virtual coils using one or more of principle component analysis, independent component analysis, kernel principal component analysis, machine learning, or deep learning.

The method may include compressing the coil dimensions to a fixed and predetermined number of virtual coils using a coil compression engine.

The coil compression engine may be incorporated as part of the artificial intelligence engine.

The coil compression engine may be a convolutional layer of the artificial intelligence engine.

The artificial intelligence engine may include one or more of a deep learning model including one or more gated recurrent units, long short term memory networks, fully convolutional neural network models, generative adversarial networks, back propagation neural network models, radial basis function neural network models, deep belief nets neural network models, or Elman neural network models.

According to an aspect of the present disclosure a system includes a multi-coil MRI data source, a coil compression engine configured to compress multi-coil dimensioned MRI data from the multi-coil MRI data source to a fixed and predetermined number of virtual coils, and an artificial intelligence engine that utilizes the fixed and predetermined number of virtual coils for artificial intelligence applications.

These and other aspects, implementation forms, and advantages of the exemplary embodiments will become apparent from the embodiments described herein considered in conjunction with the accompanying drawings. It is to be understood, however, that the description and drawings are designed solely for purposes of illustration and not as a definition of the limits of the disclosed invention, for which reference should be made to the appended claims. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

BRIEF DESCRIPTION OF THE DRAWINGS

In the following detailed portion of the present disclosure, the invention will be explained in more detail with reference to the example embodiments shown in the drawings. These embodiments are non-limiting exemplary embodiments, in which like reference numerals represent similar structures throughout the several views of the drawings, wherein.

DETAILED DESCRIPTION

Figure 1:
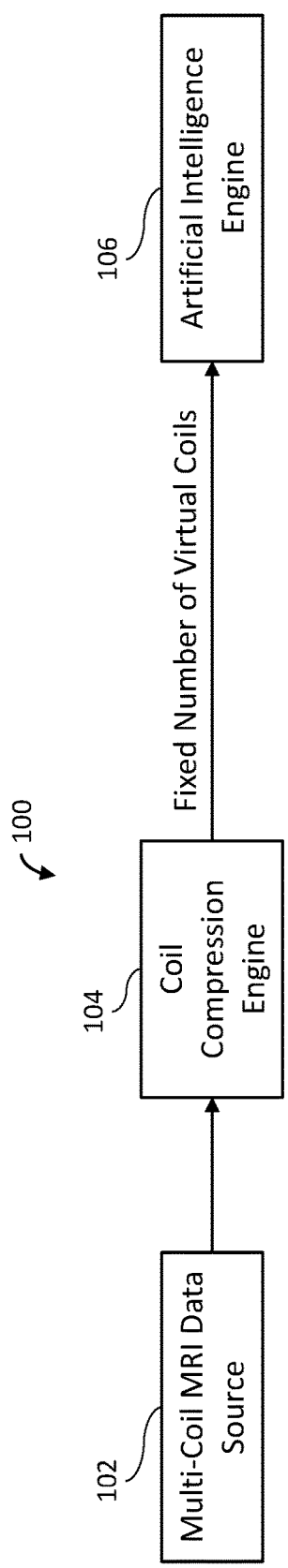
FIG. 1 illustrates an exemplary process flow according to aspects of the disclosed embodiments.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirits and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by other expression if they may achieve the same purpose.

It will be understood that when a unit, module or block is referred to as being "on," "connected to" or "coupled to" another unit, module, or block, it may be directly on, connected or coupled to the other unit, module, or block, or intervening unit, module, or block may be present, unless the context clearly indicates otherwise. As used herein, the term "and/or" includes any and all combinations of one or more of the associated listed items.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an Erasable Programmable Read Only Memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The disclosed embodiments may generally utilize coil compression to enable practical application of artificial intelligence methods for multi-coil MRI. The disclosed embodiments may also utilize coil compression to address the issues associated with using artificial intelligence methods for multi-coil MRI, for example, memory requirements, computational speed, training complexity and neural network capability. The disclosed embodiments may further utilize coil compression to exploit the redundancy among coils and calculate a linear or non-linear transform that can sparsify the data along a fixed, predetermined coil dimension, resulting in a fixed and predetermined number of virtual coils that carry most of the information. Where the MRI data is acquired from a number of coils that is smaller than the pre-determined number of virtual coils, exemplary operations such as padding zeros may be used to increase the number of virtual coils to the pre-determined number. Where the MRI data is acquired from a number of coils coil that is the same as the pre-determined number of virtual coils, exemplary operations may be utilized that output the data as input, or operations may be utilized that may compress the MRI data to the same number of virtual coils as input. Exemplary methods such as dimension reduction by principal component analysis (PCA) may be utilized for coil compression where the MRI data is acquired from a number of coils that is larger than the pre-determined number of virtual coils.

The disclosed embodiments are directed to a method comprising acquiring multi-coil MRI data, using an algorithm to compress MRI data from any number of coils to a fixed number of virtual coils, and providing the fixed number of virtual coils to a neural network for further processing.

The disclosed embodiments are further directed to a system comprising a source of multi-coil MRI data, a coil compression engine operating to compress the multi-coil MRI data to a fixed number of virtual coils, and a neural network to process the fixed number virtual coil data.

Referring to FIG. 1, a schematic block diagram of an exemplary system 100 incorporating aspects of the disclosed embodiments is illustrated. The system may include a multi-coil MRI data source 102 for providing MRI data from any number of coil assemblies. A coil compression engine 104 may receive the multi-coil MRI data and may operate to compress the multi-coil MRI data to a fixed number of virtual coils whether the number of actual coils is lager, smaller, or the same as the fixed number of virtual coils. The multi-coil MRI data, compressed to a fixed number of virtual coils, may be provided to an artificial intelligence engine 106 for various processing operations. It should be understood that the coil compression engine 104 and the artificial intelligence engine 106 of the exemplary system 100 may be implemented in hardware, software, or a combination of hardware and software.

Figure 2:
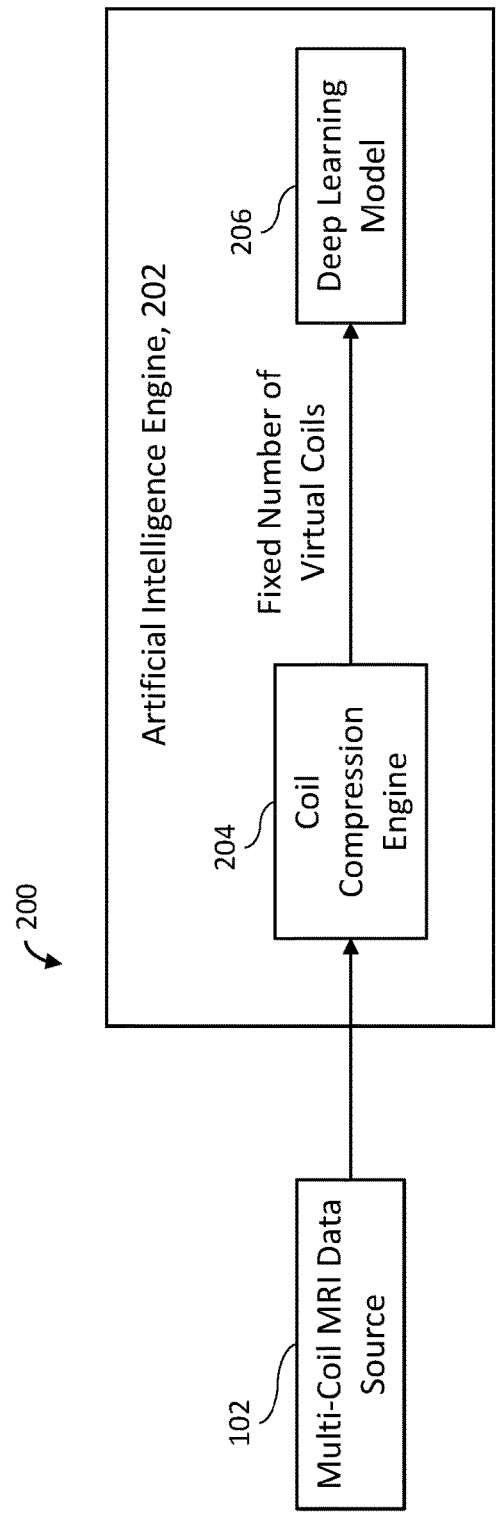
FIG. 2 illustrates an embodiment of an exemplary system incorporating aspects of the disclosed embodiments.

FIG. 2 illustrates an embodiment of an exemplary system 200 incorporating aspects of the disclosed embodiments. The system may include a multi-coil MRI data source 102 for providing MRI data from any number of coil assemblies. A coil compression engine 204 may receive the multi-coil MRI data and may operate to compress the multi-coil MRI data to a fixed number of virtual coils, however in this embodiment, the coil compression engine 204 may be incorporated as part of the artificial intelligence engine 202 and may provide the multi-coil MRI data, compressed to a fixed number of virtual coils, to another section of the artificial intelligence engine, for example, a deep learning model 206. The artificial intelligence engine 202 may be implemented in hardware, software, or a combination of hardware and software.

Figure 3:
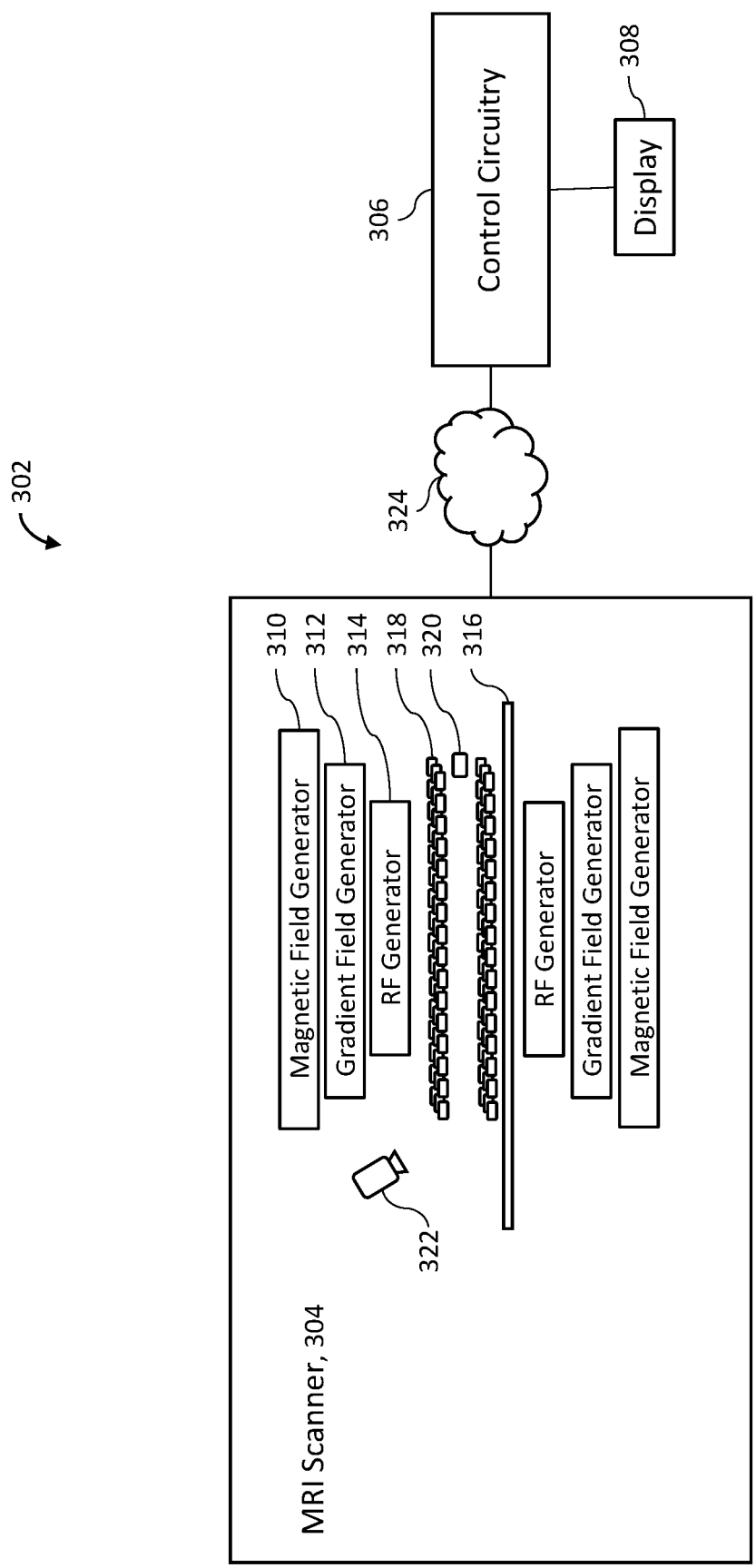
FIG. 3 shows a schematic block diagram of an exemplary multi-coil MRI data source according to the disclosed embodiments.

FIG. 3 shows a schematic block diagram of an exemplary multi-coil MRI data source 102 in the form of an MRI apparatus 302 for providing multi-coil MRI data according to the disclosed embodiments. The MRI apparatus 302 may include an MRI scanner 304, control circuitry 306 and a display 308. The function, size, type, geometry, position, amount, or magnitude of the MRI scanner 304 may be determined or changed according to one or more specific conditions. For example, the MRI scanner 304 may be designed to surround a subject (or a region of the subject) to form a tunnel type MRI scanner, referred to as a closed bore MRI scanner, or an open MRI scanner, referred to as an open-bore MRI scanner. The MRI scanner 302 may include, as shown in cross section in FIG. 3, a magnetic field generator 310, a gradient magnetic field generator 312, and a Radio Frequency (RF) generator 314, all surrounding a table 316 on which subjects under study may be positioned. The MRI scanner 304 may also include one or more coil arrays 318, an ECG signal sensor 320 for capturing MRI data in the form of ECG signals from the subject under study during MRI scanning, and a camera 322 for capturing MRI data in the form of video images of the subject under study during MRI scanning.

In some embodiments, the MRI scanner 304 may perform a scan on a subject or a region of the subject. The subject may be, for example, a human body or other animal body. In some embodiments, the subject may be a patient. The region of the subject may include part of the subject. For example, the region of the subject may include a tissue of the patient. The tissue may include, for example, lung, prostate, breast, colon, rectum, bladder, ovary, skin, liver, spine, bone, pancreas, cervix, lymph, thyroid, spleen, adrenal gland, salivary gland, sebaceous gland, testis, thymus gland, penis, uterus, trachea, skeletal muscle, smooth muscle, heart, etc. In some embodiments, the scan may be a pre-scan for calibrating an imaging scan. In some embodiments, the scan may be an imaging scan for generating an image.

The main magnetic field generator 310 may create a static magnetic field $B_0$ and may include, for example, a permanent magnet, a superconducting electromagnet, a resistive electromagnet, or any magnetic field generation device suitable for generating a static magnetic field. The gradient magnet field generator 312 may use coils to generate a magnetic field in the same direction as $B_0$ but with a gradient in one or more directions, for example, along X, Y, or Z axes in a coordinate system of the MRI scanner 304.

In some embodiments, the RF generator 314 may use RF coils to transmit RF energy through the subject, or region of interest of the subject, to induce electrical signals in the region of interest. The resulting RF field is typically referred to as the B1 field and combines with the B0 field to generate MR signals that are spatially localized and encoded by the gradient magnetic field. The coil arrays 318 may generally operate to sense the RF field and convey a corresponding output to the control circuitry 306. In some embodiments, the coil arrays may operate to both transmit and receive RF energy, while in other embodiments, the coil arrays may operate as receive only.

Figure 4A:
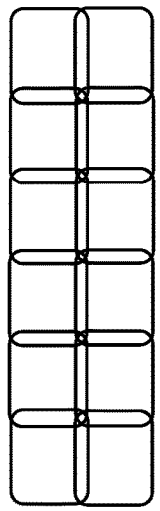
FIGS. 4A and 4B illustrate different MRI coil arrangements according to the disclosed embodiments.
Figure 4B:
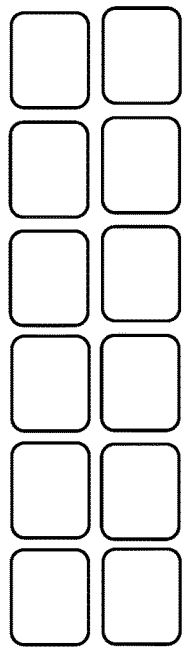

FIGS. 4A and 4B illustrate different MRI coil arrangements. The coil arrangements may include phased array coil arrangements and parallel array coil arrangements. FIG. 4A shows an exemplary phased array coil arrangement where the coils overlap and are coupled together to enhance gain and signal to noise properties. FIG. 4B shows an exemplary parallel array arrangement where the coils are decoupled and optimized for parallel imaging. The coil arrangements may include any number of coils, depending on a particular application. Exemplary numbers of coils may include 12, 16, 24, 32, 64 or more.

Returning to FIG. 3, the control circuitry 306 may control overall operations of the MRI scanner 304, in particular, the magnetic field generator 310, the gradient magnetic field generator 312, the RF generator 314, and the coil arrays 318. For example, the control circuitry 306 may control the magnet field gradient generator to produce gradient fields along one or more of the X, Y, and Z axes, and the RF generator to generate the RF field. In some embodiments, the control circuitry 306 may receive commands from, for example, a user or another system, and control the magnetic field generator 310, the gradient magnetic field generator 312, the RF generator 314, and the coil arrays 318 accordingly.

The control circuitry 306 may be connected to the MRI scanner 304 through a network 324. The network 324 may include any suitable network that can facilitate the exchange of information and/or data for the MRI scanner 304. The network 324 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 324 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 324 may include one or more network access points. For example, the network 324 may include wired and/or wireless network access points such as base stations and/or internet exchange points through which one or more components of the MRI scanner 402 may be connected with the network 324 to exchange data and/or information.

According to some embodiments, the coil compression engine 104 and the artificial intelligence engine 106 may be incorporated in the control circuitry 306, while in other embodiments, one or both of the coil compression engine 104 and the artificial intelligence engine 106 may be located remotely from the control circuitry 306.

Figure 5:
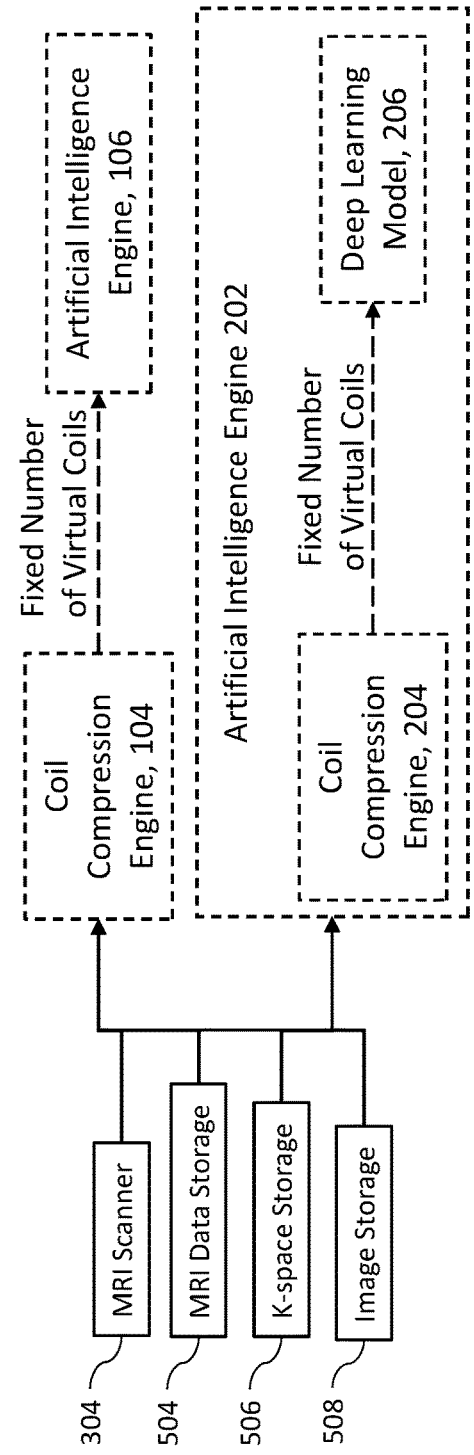
FIG. 5 shows various exemplary embodiments of MRI data sources for implementing the disclosed embodiments.

FIG. 5 shows various exemplary embodiments of MRI data sources for implementing the disclosed embodiments. The sources of MRI data may include, without limitation, one or more of the MRI scanner 304, a storage of multi-coil MRI data 504, for example, MRI slices or other MRI apparatus output, a storage of multi-coil k-space data 506 from any number of MRI scans, and an image storage 508 of multi-coil MRI images, or any other suitable source of multi-coil MRI data. The MRI data sources may further include any number of local, remote, or cloud based sources.

Figure 6:
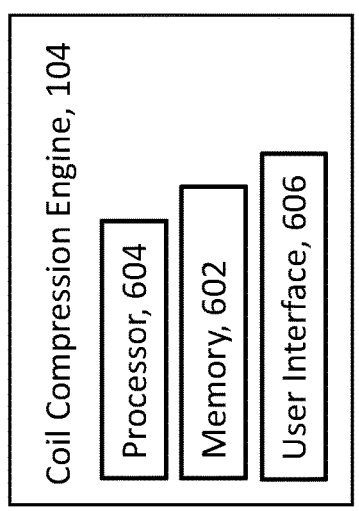
FIG. 6 illustrates an exemplary architecture of a coil compression engine according to the disclosed embodiments.

FIG. 6 illustrates an exemplary architecture of the coil compression engine 104 according to the disclosed embodiments. The coil compression engine 104 may include computer readable program code stored on at least one computer readable medium 602 for carrying out and executing the process steps described herein. The computer readable program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The computer readable program code may execute entirely on the coil compression engine 104, partly on the coil compression engine 104, as a stand-alone software package, partly on the coil compression engine 104 and partly on a remote computer or server or entirely on the remote computer or server. In the latter scenario, the remote computer may be connected to the coil compression engine 104 through any type of network, including those mentioned above with respect to network 324.

The computer readable medium 602 may be a memory of the coil compression engine 104. In alternate aspects, the computer readable program code may be stored in a memory external to, or remote from, the coil compression engine 104. The memory may include magnetic media, semiconductor media, optical media, or any media which is readable and executable by a computer. The coil compression engine 104 may also include a computer processor 604 for executing the computer readable program code stored on the at least one computer readable medium 602. In at least one aspect, the coil compression engine 104 may include one or more input or output devices, generally referred to as a user interface 606 which may operate to allow input to the coil compression engine 104 or to provide output from the coil compression engine 104, respectively. The coil compression engine 104 may be implemented in hardware, software or a combination of hardware and software.

The coil compression engine 104 generally operates to linearly or nonlinearly combine raw data from a variable number of multiple coils, depending on the MRI scanner producing the MRI data, into a fixed number of virtual coils. Exemplary fixed numbers of virtual coils may generally be between 4 and 20, however, it should be understood that any fixed number of virtual coils may be utilized. The coil compression engine 104 may utilize any number of various compression techniques including, but not limited to Principle Component Analysis (PCA), Independent Component Analysis (ICA), Kernel Principal Component Analysis (KPCA), Machine Learning (ML), Deep Learning (DL). In some embodiments, to perform the coil compression, a $n_{calib} \times n_{calib}$ central region of the k-space of every coil representing low-spatial-frequency component $y_{calib} \in C^{n_{calib}^2 \times n_c}$ is used as the calibration data. The calibration data is factorized using singular value decomposition and the first $n_{vc}$ columns of the right-singular vectors are kept to form a compression matrix $M_c \in C^{n_c \times n_{vc}}$. The acquired $n_c$-coil data is then compressed to $n_{vc}$ virtual coils through $y_{comp} = y \cdot M_c$, where · represents the matrix multiplication and y is rearranged into shape $n \times n_c$ before multiplying.

Referring again to FIG. 2, when incorporated as part of the artificial intelligence engine 202, the coil compression engine 205 can be implemented as a pre-learned convolutional layer with a 1×1 kernel size. Each column of the compression matrix is a filter and there are total $n_{vc}$ filters, which convert the input $n_c$ channel data to $n_{vc}$ channel features.

Figure 7:
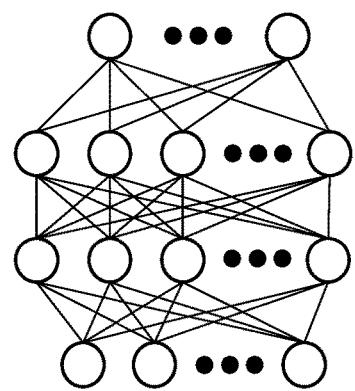
FIG. 7 depicts an exemplary neural network that may be utilized to implement the disclosed embodiments.

FIG. 7 depicts an exemplary simple neural network 700 that may be utilized to implement the disclosed embodiments. While a simple neural network is shown, it should be understood that the disclosed embodiments may be implemented utilizing a deep learning model including one or more gated recurrent units (GRUs), long short term memory (LSTM) networks, fully convolutional neural network (FCN) models, generative adversarial networks (GANs), back propagation (BP) neural network models, radial basis function (RBF) neural network models, deep belief nets (DBN) neural network models, Elman neural network models, or any deep learning or machine learning model capable of performing the operations described herein. The multi-coil MRI data, compressed to a fixed number of virtual coils may be used to train the neural network 700. In one embodiment, the neural network 700 may operate to recover image information from acquired multi-coil k-space data, where the data may be undersampled for acceleration purpose. In another embodiment, the neural network may operate to perform post-processing such as denoising of the acquired multi-coil k-space or image data. When incorporated as part of the artificial intelligence engine 202, the coil compression engine 205 may be implemented as a special layer in the deep learning model 206 or the neural network 700.

The number of the virtual coil dimensions can be determined by experiments or experiences, or be learned from the data as a hyperparameter. One example of deciding virtual coil number from experiments or experiences is to calculate the total energy maintained in the compressed data. The total energy can be calculated using the Frobenius norm of the data matrix resulting from the coil compression operation. The same technique may be used to calculate the energy of the original uncompressed data from the multi-coil MRI data source, and the total energy of the compressed signal at different compression rates may also be calculated. Given the nature of the compression, the remaining energy after compression may be represented as a monotonic curve that increases as the number of virtual coils increases. A threshold value of the remaining energy after compression can be determined heuristically, where the threshold value is sufficient for subsequent applications, while at the same time allowing for filtering unnecessary energy that is mostly noise. The number of virtual coils that meet the determined threshold value of the remaining energy after compression may then be selected. In some embodiments, the selected number of virtual coils may be fixed and added to the neural network 700 and the compression layer parameters may not update during the training of the neural network. In another embodiment, the number of virtual coils may not be fixed and added to the neural network. The compression layer parameters are initialized using the pre-calculated parameters and are updated along with the other parts of the neural network 700 during training.

Techniques that train to learn or to select a particular neural network structure can be used to learn the hyperparameter of the neural network for optimal performance. One example following a reinforcement learning framework can be a searching neural network that can act on the tested neural network by changing the hyperparameters and observing the resulting performance. The searching network can continuously perform trials of acting and observing, and accumulate experiences through the trials. The target of the searching network is to maximize some reward, which can be defined as achieving better performance. The searching network will eventually reach an optimal performance point, at which the operations of the searching network may be terminated.

Figure 8:
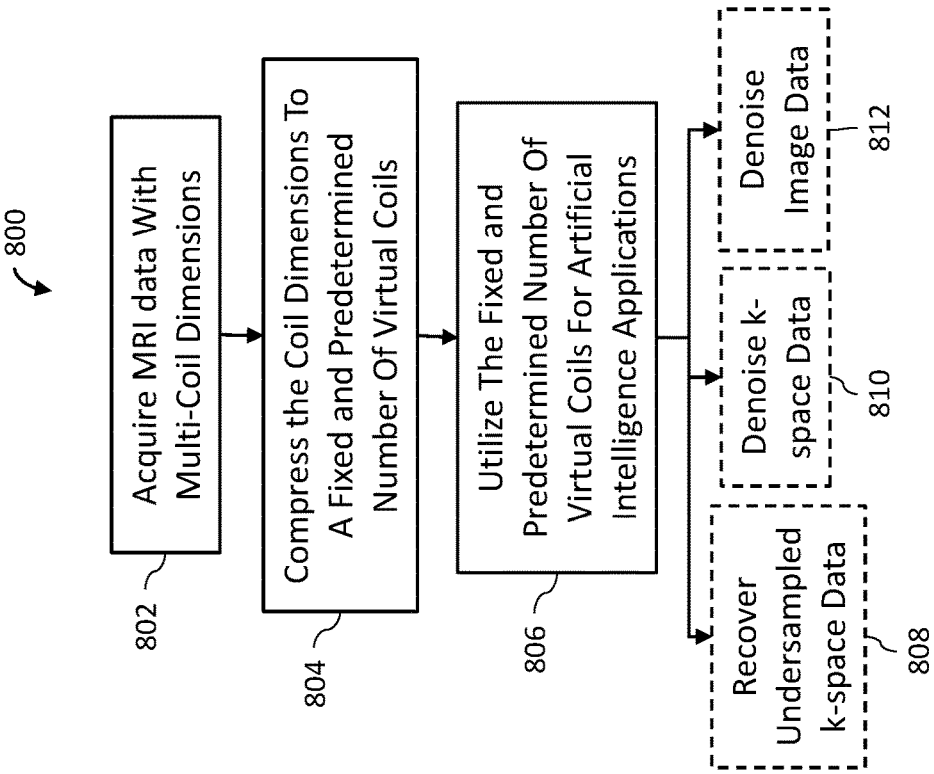
FIG. 8 shows an exemplary procedure for utilizing a multi-coil MRI data source, a coil compression engine, and an artificial intelligence engine according to the disclosed embodiments.

FIG. 8 shows an exemplary procedure 800 for utilizing the multi-coil MRI data source 302, the coil compression engine 104, 204 and the artificial intelligence engine 106, 202 according to the disclosed embodiments. As shown in block 802, multi-coil MRI data may be acquired from any suitable source, for example, one or more of the MRI scanner 304, the storage of multi-coil MRI data 504, for example, MRI slices or other MRI apparatus output, the storage of multi-coil k-space data 506 from any number of MRI scans, and the image storage 508 of multi-coil MRI images. The multi-coil MRI data may be derived from any suitable number of MRI coils, for example, 12, 16, 24, 32, 64 or more. As shown in block 804, the coil dimensions of the multi-coil data may be compressed to a fixed and pre-determined number of virtual coils. In some embodiments, the fixed and predetermined number of virtual coils may be any suitable number, for example, 10 or less. As shown in block 806, the fixed and predetermined number of virtual coils may be used by the artificial intelligence engine 106, 202 for various applications, for example, recovering undersampled k-space data 808, denoising k-space data 810, and denoising image data 812.

The proposed method will result in no difference in the training or testing of the artificial intelligence engine 106, 202 in order to accomplish these exemplary applications. The neural network with the proposed coil compression "layer" can be formed as supervised, semi-supervised or unsupervised, can use any kinds of loss, and can be trained using different kinds of training strategy, so long as the application utilizes multi-coil data.

In order to accomplish artificial intelligence applications, the artificial intelligence engine 106 may be trained to reconstruct MR images from acquired multi-coil k-space data in a supervised manner. The input to the artificial intelligence engine 106 may be the multi-coil k-space data and the resulting output of the artificial intelligence engine 106 may be estimated images. The estimated images may be compared to ground truth images and the differences between the estimated images and the ground truth images may be back-propagated to update the parameters of the neural network 700 in the artificial intelligence engine 106 to improve the accuracy of the estimations. Testing of the neural network 700 in the artificial intelligence engine 106 may be performed without ground truth images and the input multi-coil k-space data may be fed to the trained neural network which may then output estimated reconstructions. For the artificial intelligence engine 202 with the coil compression engine 204 implemented as a layer of the deep learning model 206 or the neural network 700, the input, the output, the ground truths and the training and testing processes may be the same as for the artificial intelligence engine 106 separate from the coil compression engine 104. The input multi-coil k-space data may be provided to the compression layer where the dimension of the multi-coil k-space data may be compressed to a fixed number. This compressed data may be further fed to the preceding layers in the neural network 700. During training, the difference between the estimations and the ground truths may be back-propagated to update the parameters of the neural network 700. During testing, the input multi-coil k-space data may be fed to the trained neural network which may then output estimated reconstructions.

The compression of a variable coil dimension to a fixed and predetermined virtual coil dimension may generally result in less constraints on the design of the neural network. The trained neural network is presented with a fixed coil dimension, regardless of the number of coils from which data may be collected, which greatly increases the flexibility of the artificial intelligence engine design. The compressed coil number is typically smaller, for example, less than 10, than the number of coils utilized for the MRI scan, requiring less memory for testing the neural network. The smaller memory also allows for training a larger and more complex neural network, and the smaller number of coils results in a faster inference time for the neural network. The signals from each virtual coil may exhibit a higher signal to noise ratio than the actual physical coils and may translate to the ability of the neural network to learn more representative features of the MRI data and better image quality.

Thus, while there have been shown, described and pointed out, fundamental novel features of the invention as applied to the exemplary embodiments thereof, it will be understood that various omissions, substitutions and changes in the form and details of devices and methods illustrated, and in their operation, may be made by those skilled in the art without departing from the spirit and scope of the presently disclosed invention. Further, it is expressly intended that all combinations of those elements, which perform substantially the same function in substantially the same way to achieve the same results, are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method comprising:
acquiring magnetic resonance imaging (MRI) data with multi-coil dimensions;
compressing the coil dimensions to a fixed and predetermined number of virtual coils by:
using a central region of a k-space of each coil dimension as calibration data;
factorizing the calibration data using single value decomposition to form a compression matrix; and
multiplying each coil dimension by the compression matrix;
the method further comprising utilizing the fixed and predetermined number of virtual coils by an artificial intelligence engine for artificial intelligence applications.

2. The method of claim 1, comprising acquiring the MRI data with multi-coil dimensions from one or more of an MRI scanner, an MRI data storage, a k-space storage, or an image storage.

3. The method of claim 1, wherein the multi-coil dimensions comprise 12, 16, 24, 32, or 64 coils.

4. The method of claim 1, wherein the fixed and predetermined number of virtual coils is between 4 and 20.

5. The method of claim 1, comprising compressing the coil dimensions to a fixed and predetermined number of virtual coils using one or more of principle component analysis, independent component analysis, kernel principal component analysis, machine learning, or deep learning.

6. The method of claim 1, comprising compressing the coil dimensions to a fixed and predetermined number of virtual coils using a coil compression engine.

7. The method of claim 6, wherein the coil compression engine is incorporated as part of the artificial intelligence engine.

8. The method of claim 7, wherein the coil compression engine comprises a convolutional layer of the artificial intelligence engine.

9. The method of claim 1, wherein the artificial intelligence engine comprises one or more of a deep learning model including one or more gated recurrent units, long short term memory networks, fully convolutional neural network models, generative adversarial networks, back propagation neural network models, radial basis function neural network models, deep belief nets neural network models, or Elman neural network models.

10. The method of claim 1, wherein the artificial intelligence applications comprise one or more of recovering image information from undersampled multi-coil k-space data, denoising of multi-coil k-space data, or denoising image data.

11. A system comprising:
a multi-coil MRI data source;
a coil compression engine configured to compress multi-coil dimensioned MRI data from the multi-coil MRI data source to a fixed and predetermined number of virtual coils by:
using a central region of a k-space of each coil dimension as calibration data;
factorizing the calibration data using single value decomposition to form a compression matrix; and
multiplying each coil dimension by the compression matrix;
an artificial intelligence engine that utilizes the fixed and predetermined number of virtual coils for artificial intelligence applications.

12. The system of claim 11, wherein the MRI data is acquired from one or more of an MRI scanner, an MRI data storage, a k-space storage, or an image storage.

13. The system of claim 11, wherein the multi-coil dimensions comprise 12, 16, 24, 32, or 64 coils.

14. The system of claim 11, wherein the fixed and predetermined number of virtual coils is between 4 and 20.

15. The system of claim 11, wherein the coil compression engine is configured to compress the coil dimensions to a fixed and predetermined number of virtual coils using one or more of principle component analysis, independent component analysis, kernel principal component analysis, machine learning, or deep learning.

16. The system of claim 11, wherein the coil compression engine is incorporated as part of the artificial intelligence engine.

17. The system of claim 16, wherein the coil compression engine comprises a convolutional layer of the artificial intelligence engine.

18. The system of claim 11, wherein the artificial intelligence engine comprises one or more of a deep learning model including one or more gated recurrent units, long short term memory networks, fully convolutional neural network models, generative adversarial networks, back propagation neural network models, radial basis function neural network models, deep belief nets neural network models, or Elman neural network models.

19. The system of claim 11, wherein the artificial intelligence applications comprise one or more of recovering image information from undersampled multi-coil k-space data, denoising of multi-coil k-space data, or denoising image data.

* * * * *